(12) United States Patent
Olson (10) Patent No.: US 7,069,075 B2
(45) Date of Patent: Jun. 27, 2006

(54) SUBCUTANEOUS IMPLANTABLE CARDIOVERTER/DEFIBRILLATOR

(75) Inventor: Walter H. Olson, North Oaks, MN (US)

(73) Assignee: Medtronic, Inc., Minneapolis, MN (US)

( * ) Notice: Subject to any disclaimer, the term of this patent is extended or adjusted under 35 U.S.C. 154(b) by 229 days.

(21) Appl. No.: 10/717,395

(22) Filed: Nov. 19, 2003

(65) Prior Publication Data

US 2005/0055056 A1 Mar. 10, 2005

Related U.S. Application Data (60) Provisional application No. 60/428,400, filed on Nov. 22, 2002.

(51) Int. Cl.
*A61N 1/39* (2006.01)
(52) U.S. Cl. .................. 607/5; 607/4; 607/36; 607/129
(58) Field of Classification Search .................... 607/4, 607/5, 36, 129, 152
See application file for complete search history.

(56) References Cited

U.S. PATENT DOCUMENTS

| | | | |
|---|---|---|---|
| 4,877,032 A | * | 10/1989 | Heinze et al. .................. 607/2 |
| 5,163,427 A | | 11/1992 | Keimel |
| 5,188,105 A | | 2/1993 | Keimel |
| 5,193,535 A | | 3/1993 | Bardy et al. |
| 5,255,692 A | | 10/1993 | Neubauer et al. |
| 5,314,451 A | | 5/1994 | Mulier |
| 5,342,407 A | | 8/1994 | Dahl et al. |
| 5,645,586 A | * | 7/1997 | Meltzer .................. 623/11.11 |
| 5,991,656 A | | 11/1999 | Olson et al. |
| 6,280,462 B1 | | 8/2001 | Hauser et al. .................. 607/5 |

(Continued)

FOREIGN PATENT DOCUMENTS

| | | |
|---|---|---|
| WO | WO 95/09661 | 4/1995 |

(Continued)

OTHER PUBLICATIONS

Gradaus, Rainer, et al., "Nonthoractomy Implantable Cardioverter Defibrillator Placement in Children: Use of Subcutaneous Array Leads and Abdominally Placed Implantable Cardioverter Defibrillators in Children", *Journal of Cardiovascular Electrophysiology*, vol. 12, No. 3, Mar. 2001, pp. 356-360.

(Continued)

*Primary Examiner*—Robert E. Pezzuto
*Assistant Examiner*—Tammie K. Heller
(74) *Attorney, Agent, or Firm*—Mike C. Soldner; Girma Wolde-Michael (57) ABSTRACT

Implantable cardioverter-defibrillators (ICDs) are disclosed that are entirely implantable subcutaneously with minimal surgical intrusion into the body of the patient and provide distributed cardioversion/defibrillation and pace/sense electrodes for delivery of cardioversion/defibrillation shock and pacing therapies across the heart when necessary. At least two hermetically sealed housings forming first and second hermetically sealed housings coupled together by a cable support first, second and, optionally, third cardioversion/defibrillation electrodes. The relatively bulky high voltage battery and high voltage capacitors, and circuitry powered by a low voltage power source for detecting a tachyarrhythmia, charging the high voltage capacitor, and discharging the high voltage capacitor to provide a cardioversion/defibrillation shock are distributed between the first and second hermetically sealed housings.

23 Claims, 6 Drawing Sheets

U.S. PATENT DOCUMENTS

| | | | |
|---|---|---|---|
| 6,647,292 B1 * | 11/2003 | Bardy et al. ..................... | 607/5 |
| 6,952,610 B1 * | 10/2005 | Ostroff et al. ................. | 607/14 |
| 2002/0035377 A1 | 3/2002 | Bardy et al. | |
| 2002/0042634 A1 | 4/2002 | Bardy et al. | |
| 2002/0072773 A1 | 6/2002 | Bardy et al. | |
| 2002/0103510 A1 | 8/2002 | Bardy et al. | |
| 2002/0107547 A1 | 8/2002 | Erlinger et al. | |
| 2002/0107548 A1 | 8/2002 | Bardy et al. | |
| 2002/0107559 A1 | 8/2002 | Sanders et al. ............. | 607/129 |

FOREIGN PATENT DOCUMENTS

| | | |
|---|---|---|
| WO | WO 02/24275 A2 | 8/2001 |
| WO | WO 02/02185 | 1/2002 |

OTHER PUBLICATIONS

Schuder, John C., et al., "Experimental Ventricular Defribrillation With an Automatic and Completely Implanted System", *Transactions American Society for Artificial Internal Organs,* vol. XVI, 1970, pp. 207-212.

Olson, Walter H., et al., "Onset and Stability for Ventricular Tachyarrhythmia Detection in an Implantable Pacer-Cardioverter-Defibrillator", *Computers in Cardiology,* 1986, pp. 167-170.

* cited by examiner

SUBCUTANEOUS IMPLANTABLE CARDIOVERTER/DEFIBRILLATOR

RELATED APPLICATION

The present invention claims priority and other benefits from U.S. Provisional Patent Application Ser. No. 60/428,400, filed Nov. 22, 2002, entitled "SUBCUTANEOUS IMPLANTABLE CARDIOVERTER/DEFIBRILLATOR", incorporated herein by reference in its entirety.

FIELD OF THE INVENTION

This invention relates to implantable cardioverter-defibrillators (ICDs), particularly ICDs that are entirely implantable subcutaneously or submuscularly and entirely outside the thorax with minimal surgical intrusion into the body of the patient and providing distributed cardioversion/defibrillation and pace/sense electrodes for delivery of cardioversion/defibrillation shock and pacing therapies across the heart when necessary.

BACKGROUND OF THE INVENTION

Many types of implantable medical devices (IMDs) have been clinically implanted into patient's bodies over the last twenty years that deliver relatively high-energy cardioversion and/or defibrillation shocks to a patient's heart when a malignant tachyarrhythmia, e.g., atrial or ventricular fibrillation, is detected. Cardioversion shocks are delivered in synchrony with a detected R-wave when fibrillation detection criteria are met, whereas defibrillation shocks are delivered when fibrillation criteria are met and an R-wave cannot be discerned from the EGM. The earliest clinically released automatic implantable defibrillators (AIDs) that were implanted in human patients provided a high energy defibrillation shock developed by an AID implantable pulse generator (IPG) through a pair of epicardial electrodes applied directly to the epicardium of the heart exposed through a thoracotomy when high heart rate detection criteria were met. Later developed and clinically implanted ICDs, originally referred to as pacemaker/cardioverter/defibrillators (PCDs), possessed more sophisticated detection algorithms and provided defibrillation, R-wave synchronized cardioversion, and pacing therapies to treat a variety of malignant tachyarrhythmias ranging from fibrillation to fast tachycardias. Current ICDs typically additionally possess single or dual chamber bradycardia pacing capabilities for treating specified chronic or episodic atrial and/or ventricular bradycardia and tachycardia. The most current clinically released ICDs also include right and left heart chamber pacing capabilities for improving the cardiac output of patient's hearts that are in heart failure. Unless otherwise indicated, all of the above-described IMDs are referred to herein as ICDs.

It was postulated early in the development of ICDs that cardioversion/defibrillation shocks could be delivered between large surface area patch electrodes implanted subcutaneously over the ribcage on either side of the heart as indicated in the article by Schuder et al. entitled "Experimental Ventricular Defibrillation with an Automatic and Completely Implanted System", *Transactions American Society for Artificial Internal Organs*, 16:207, 1970. Others postulated that atrial and ventricular cardioversion/defibrillation shocks could more advantageously be applied across a fibrillating atrial or ventricular heart chamber between an epicardial electrode or the conductive case of the AID IPG and a cardioversion/defibrillation shock electrode lodged into the right atrium or ventricle, respectively, at the end of an endocardial lead advanced transvenously into the heart chamber. However, it was not possible to realize such an arrangement using lead technologies available at that time, and so the epicardial cardioversion/defibrillation electrodes were implanted initially.

The cardioversion/defibrillation leads employed with ICDs have evolved due to improvements that have been made in lead conductors capable of carrying relatively high cardioversion/defibrillation currents, electrode materials and configurations capable of distributing the energy with respect to a heart chamber, and insulating materials capable of withstanding breakdown when subjected to such energies. In particular, great strides have been made in developing small diameter, endocardial leads bearing elongated cardioversion/defibrillation electrodes that can be placed in the right heart chamber and/or into the coronary sinus that have reduced the cardioversion/defibrillation energy required to cardiovert/defibrillate the heart. Presently, clinically implanted ICDs are typically implanted with one or more endocardial lead lodging one or more cardioversion/defibrillation and pace/sense electrodes in one or more heart chamber and coronary vessel, e.g., the coronary sinus and vessels branching therefrom, in conjunction with use of the ICD IPG housing or "can" electrode or a further subcutaneous cardioversion/defibrillation electrode as a further remote electrode.

The implantation of such endocardial cardioversion/defibrillation electrodes used in conjunction with subcutaneous cardioversion/defibrillation electrodes does eliminate the trauma associated with surgically accessing the epicardial surface to implant epicardial cardioversion/defibrillation electrodes. Nevertheless, it has long been appreciated that the subcutaneous implantation of the ICD and all of the associated cardioversion/defibrillation leads and electrodes would also advantageously simplify the procedure and reduce the expense of implantation.

Consequently, the possibility of implanting at least two large surface area cardioversion/defibrillation electrodes subcutaneously and coupling the electrodes to a subcutaneously implanted ICD IPG has been revisited on a number of occasions since the first such implantation by Schuder. For example, the disclosures of U.S. Pat. Nos. 5,255,692 and 5,342,407 and in U.S. Patent Application Publication Nos. 2002/0042634 and 2002/0035377 to Bardy et al., evidence such continued interest.

In the '407 patent, the disclosed defibrillation system includes an IPG and a pair of leads connecting the IPG to defibrillation electrodes that are implanted subcutaneously outside of the rib cage in the thoracic region on opposite sides of the heart. More particularly, one defibrillation electrode is subcutaneously implanted to the left of, and anterior with respect to, the heart, and the other defibrillation electrode is subcutaneously implanted posterior with respect to the heart, and to the right of the heart. The IPG is also implanted anterior and to the left of heart, below one of the subcutaneous defibrillation electrodes. The IPG can incorporate circuitry for sensing cardiac electrical activity, in which case the same large surface area, subcutaneous defibrillation electrodes are used for sensing such activity as well as delivering defibrillation pulses.

A similar defibrillation system is disclosed in the '692 patent, except that the defibrillation electrodes are shaped and sized to conform to an interspace between the periost and the bone at the inner side of a rib proximal to the heart, e.g. the fourth rib. The shaped defibrillation electrodes also have a fixation mechanism that engages the ribs and is used to maintain the electrode in position chronically.

The above-referenced Bardy et al. applications disclose subcutaneously implanted ICD IPGs that are coupled with at least one cardioversion/defibrillation lead. In certain embodiments, the ICD IPG has a conventional configuration having a can electrode that functions as one cardioversion/defibrillation electrode and is implanted subcutaneously anterior or posterior to the heart. The cardioversion/defibrillation lead is tunnelled subcutaneously under the skin and around the thorax to locate the lead supported cardioversion/defibrillation electrode posterior or anterior to the heart, respectively. In certain embodiments, two cardioversion/defibrillation leads that are electrically connected together are tunnelled subcutaneously under the skin and around the thorax to locate the two cardioversion/defibrillation electrodes apart from one another and posterior or anterior to the heart, respectively. Electrical sensing of the cardiac EGM is accomplished across two sense electrodes displaced apart from one another on the IPG housing. Cardioversion/defibrillation shocks are delivered across the thorax between the cardioversion/defibrillation electrodes on the IPG housing and the lead. It is also asserted that cardiac pacing pulses can be applied to the heart across the cardioversion/defibrillation electrodes on the IPG housing and the lead. In certain embodiments, the IPG housing is shaped in an elongated, thin, narrow shape to approximate and conform to the curvature of the thorax for cosmetic reasons and in some cases to fit between the ribs, e.g., between the fourth and fifth ribs.

In commonly assigned U.S. Pat. No. 5,314,451, an ICD IPG is disclosed that is adapted to be coupled to a three-conductor cardioversion/defibrillation lead of any of the known types. The ICD IPG is formed in two separate hermetically sealed housings or cans that are coupled together by a power delivery cable. A first hermetically sealed can encloses the electronic circuitry of the ICD as well as the small volume, long-lived pacing and sensing battery, and the second hermetically sealed can encloses the high voltage, large volume cardioversion/defibrillation shock battery. The second can enclosing the large volume cardioversion/defibrillation shock battery can be readily surgically accessed and replaced upon depletion of the large volume cardioversion/defibrillation shock battery while leaving the cardioversion/defibrillation lead and the first can enclosing the IPG circuitry undisturbed. The cardioversion/defibrillation leads coupled with the first can extend transvenously into a heart chamber or cardiac vessel. Pacing and cardioversion/defibrillation therapies are generated by the electronic circuitry of the first can and delivered to the heart through pace/sense and cardioversion/defibrillation electrodes on the lead and a common electrode on the surface of the first can in any of the conventional manners.

In one disclosed embodiment, a first cardioversion/defibrillation electrode is formed on the first can and a second cardioversion/defibrillation electrode is formed on the second can. The first and second cans are adapted to be implanted subcutaneously in the thoracic region, whereby the first and second cardioversion/defibrillation electrodes are disposed apart from one another and with respect to the heart. How cardioversion/defibrillation shocks are delivered employing the first and second cardioversion/defibrillation electrodes is not explained, but the first and second cardioversion/defibrillation electrodes could be electrically coupled to the COMMON output of the high voltage output circuitry to be used in conjunction with biphasic shocks delivered from the HV-1 and HV-2 terminals between the commonly connected subcutaneous cardioversion/defibrillation electrodes and the cardioversion/defibrillation electrode on the lead inserted into the heart chamber.

There are a number of appreciable drawbacks to simply delivering cardioversion/defibrillation shocks between subcutaneously implanted cardioversion/defibrillation electrodes of the types described in these patents and applications. First of all, the energy demands on the high voltage cardioversion/defibrillation battery and the low voltage pace/sense battery are magnified considerably by the additional impedance presented by the body tissue and fluids between the spaced apart subcutaneous electrodes. Pacing pulse energies may have to be increased ten-fold to capture the heart. Pacing at these high energies is known to be painful. And, only simple ventricular pacing algorithms may be usable to overdrive the heart. Similarly, the magnitude of cardioversion/defibrillation shocks may be such as to be extremely painful to the patient, if the patient is still conscious when the shock is delivered. On the other hand, there are several reasons why a simple, inexpensive, subcutaneously implanted ICD would be of benefit.

First of all, highly sophisticated testing and monitoring equipment and trained electrophysiologists are presently required to implant the current highly sophisticated and expensive ICDs. Electrophysiologists or specialized cardiologists are required to work up the patient, particularly to induce a malignant tachyarrhythmia, e.g., fibrillation, so as to ascertain the parameter of the arrhythmia detection algorithms that will reliably result in a declared tachyarrhythmia, to ascertain which therapies are to be delivered that will reliably cardiovert or defibrillate the heart in response to the declared tachyarrhythmia, the shock energy of each delivered cardioversion/defibrillation shock or other therapy that is to be delivered, and to otherwise perform the surgical procedure. There are not enough trained electrophysiologists or cardiologists to perform these procedures, particularly in less developed countries. And, the ICD cost and procedure cost must be reduced to make the therapy available in such countries.

Therefore, a need exists for simplified and less expensive ICDs that can be implanted by cardiologists and general surgeons to meet the needs of such population groups.

Secondly, because such ICDs and procedures are highly expensive, most patients in developed countries who receive the same have experienced and survived a sudden death episode. Survivors of sudden death episodes are in the minority, and so studies are ongoing to identify patients who are asymptomatic by conventional measures but are nevertheless at risk of sudden death. Current studies of patient populations, e.g., the MADIT II and SCDHeFT studies are establishing that there large numbers of patients in any given population that are susceptible to sudden death and that they can be identified with some degree of certainty. However, implanting currently available ICDs in all such patients would be prohibitively expensive.

Therefore, a need exists for an inexpensive, simplified, prophylactic ICD that can be subcutaneously implanted in such patients in the expectation that the patient may at some time suffer a sudden death episode, causing the ICD to deliver the appropriate cardioversion/defibrillation shock and possibly to deliver post-shock pacing, if necessary. Such a subcutaneously implanted ICD would likely be capable of delivering a limited number of cardioversion/defibrillation shocks at maximal shock energy and deliver pacing pulses for a few minutes time. In this way, the patient can be assured of surviving the first sudden death episode. The prophylactic ICD in a surviving patient would then be replaced by the more sophisticated, longer-lived current ICD.

There are also pediatric patients whose hearts are too small or are naturally growing and cannot accommodate transvenous cardioversion/defibrillation leads. In certain cases, cardioversion/defibrillation leads have been implanted subcutaneously rather than in the heart chambers in such patients. See Gradaus et al., "Nonthoracotomy implantable cardioverter defibrillator placement in children: use of subcutaneous array leads and abdominally placed implantable cardioverter defibrillators in children", *J. Cardiovasc Electrophysiol,* 12: 356–60, 2001.

Current ICD IPGs are relatively heavy and bulky compared with pacemaker IPGs despite substantial reductions in weight and volume that have been achieved over the years since the first AID IPGs were implanted. The ICD IPG comprises the hermetically sealed housing and a connector header or block attached to the housing for making connection with the cardioversion/defibrillation and pacing leads. The bulk of a given ICD IPG connector block depends upon the number of lead connectors and connector elements that are to be attached to it. The components within a given hermetically sealed housing that dictate its bulk and weight comprise the ICD circuitry, a relatively low voltage battery providing operating energy to the ICD circuitry and providing pacing pulse energy, a high current battery providing cardioversion/defibrillation shock energy, a charging transformer, a set of discrete diodes and high voltage capacitors that are charged through the transformer and diodes and discharged through the cardioversion/defibrillation electrodes, a telemetry antenna, feedthroughs to connector elements in the connector block, component spacers for holding the components in a sub-assembly, and an activity sensor in certain cases. The largest volume and weight of components in the typical ICD IPG include the set of high voltage capacitors, the high current battery, and the connector block. Current ICD IPGS range in weight between about 75 grams and about 115 grams and range in volume between about 36 cc and 62 cc. The weight and volume is proportional to the specified available cardioversion shock energy, which can range between about 25 joules and about 40 joules. The volume and weight of a given ICD IPG is therefore dependent upon the capacity of the high voltage battery, the specified energy output, and the projected battery life, assuming a standard number of shock deliveries and capacitor reformations per year.

Such relatively bulky and heavy ICD IPGs are normally implanted subcutaneously over the abdomen or the pectoral regions rather than between the skin and ribs of the thorax since the former regions have thicker subcutaneous fat, tissue and muscle layers. The outline of the implanted IPG housing is less apparent and cosmetically offensive to the patient. A great deal of design effort has been expended in achieving the most efficient and lowest volume shape of the ICD IPG housing, connector block, and the above-listed components within the hermetically sealed housing having as thin a profile as possible to make it as invisible and comfortable as possible after implantation.

As noted above, it has been found desirable to implant the ICD IPG between the skin and ribs in posterior or anterior implantation sites to function as one cardioversion/defibrillation electrode and to route the cardioversion/defibrillation leads connected to the IPG connector block subcutaneously around the thorax to locate the cardioversion/defibrillation electrodes at a remote subcutaneous implantation site. As further noted above, it is proposed to specifically narrow and elongate the cardioversion/defibrillation electrodes and ICD IPG housing to conform more closely to the space between the ribs than is possible with the typical cardioversion/defibrillation electrodes and ICD IPG housing. However, volumetric efficiency is sacrificed when such shape changes are made, and volume and weight of the ICD IPG may actually increase.

Therefore, for these and other reasons, a need exists for a relatively simple, cosmetically un-intrusive ICD that can be implanted beneath the skin over the ribcage with minimal trauma to the patient by surgeons employing conventional surgical instruments and monitoring equipment so as to make the implantation less expensive and more widely usable.

SUMMARY OF THE INVENTION

An ICD in accordance with the present invention is entirely implantable subcutaneously or submuscularly with minimal surgical intrusion into the body of the patient and provides distributed cardioversion/defibrillation and pace/sense electrodes for delivery of pacing and cardioversion/defibrillation shock therapies across the heart when necessary.

In accordance with the present invention, the bulky components of the ICD IPG are distributed between and enclosed within first and second hermetically sealed housings. The ICD is complete when the first and second hermetically sealed housings are tethered together by an electrical cable. The first hermetically sealed housing is implantable at a first subcutaneous implantation site in the patient's thorax, and the second hermetically sealed housing is implantable at a second subcutaneous implantation site in the patient's thorax, whereby the heart is disposed between the first and second hermetically sealed housings.

The ICD of the present invention is implanted by making at least one surgical incision into subcutaneous space between the patient's skin and ribcage, inserting the first hermetically sealed housing through the incision and advancing the first hermetically sealed housing subcutaneously to a first subcutaneous implantation site, inserting the second hermetically sealed housing through the incision and advancing the second hermetically sealed housing subcutaneously to a second subcutaneous implantation site spaced from the first subcutaneous implantation site so that the electrical cable is disposed subcutaneously between the first and second hermetically sealed housings, and closing the incision.

A preferred method for implanting the ICD of the present invention includes making two surgical incisions into subcutaneous or submuscular space and inserting the two components of the ICD into each one of the incisions. The connective element is then tunnelled between the two incisions to provide connection between the two component parts. This arrangement enables separation between a shocking, sensing electrode and the power package. More specifically, it enables physicians to locate the shocking and sensing electrode at the exact desirable location and also prevents migration of the components.

One other aspect of the dual incision arrangement includes a process by which the connecting electrical cable between the two component parts of the ICD is installed using a tunnelling device that is already inserted into the lumen of the electrode at the distal end. The preferred arrangement would be to attach a blunt dissection tip similar to the tunnelling tools known in the art, with slight modifications for subcutaneous manipulation. This arrangement enables a single-pass system for connecting two incision locations via a tunnelled pass-through communication and energy transfer space to allow passage of the connecting electrical cable between the two parts.

The ICD contemplated by the present invention is preferably structured to house the energy delivery system in one component and the remaining controls in the other. In the event the energy system needs replacing, the dual incision approach provides a superior method to chronically manage battery replacement. It would require only opening one of the two incisions while leaving the other component undisturbed. Further, this enables flexibility in locating the ICD component parts at optimally desirable positions and accommodate various sizes and shapes of patients.

In accordance with one aspect of the invention, the distributed components of the ICD circuitry are electrically connected together through the cable to generate cardioversion/defibrillation shocks. The cardioversion/defibrillation shocks are delivered between a first cardioversion/defibrillation electrode of the first hermetically sealed housing and a second cardioversion/defibrillation electrode of the second hermetically sealed housing.

In a further aspect of the invention, the first hermetically sealed housing encloses arrhythmia detection circuitry for detecting a cardiac tachyarrhythmia and cardioversion/defibrillation shock generating circuitry that generates a cardioversion/defibrillation shock in response to a detected cardiac tachyarrhythmia. The second hermetically sealed housing encloses a high current battery, and the cable tethering the first and second hermetically sealed housings together couples the high current battery and the second cardioversion/defibrillation electrode to the cardioversion/defibrillation shock generating circuitry.

In a still further aspect of the invention, the cable is removable from the second hermetically sealed housing to facilitate replacement of the second hermetically sealed housing upon depletion of the high current battery.

In another aspect of the invention, the cable supports a third cardioversion/defibrillation electrode coupled through the cable to the cardioversion/defibrillation shock generating circuitry to enable selective delivery of cardioversion/defibrillation shocks among selected pairs of the first, second and third cardioversion/defibrillation electrodes.

In yet another aspect of the invention, a two-dimensional array of EGM sense electrodes are provided on the first hermetically sealed housing and coupled to the EGM sensing circuitry to present multiple EGM sense vectors to improve sensing of cardiac signals of interest. Moreover, one or more EGM sense electrode is optionally provided on the second hermetically sealed housing and coupled by the cable to the sensing circuitry to present at least one additional EGM sense vector to improve sensing of cardiac signals of interest.

Pacing therapies are also preferably provided by pacing timing and pulse generating circuitry within the first hermetically sealed enclosure coupled with the pacing electrode pair comprising selected ones of the sense electrodes and the cardioversion/defibrillation electrodes supported by the first and second hermetically sealed housings.

Preferably, the first and second hermetically sealed housings are shaped to conform to the curvature of the thorax and to be connected by subcutaneous tunnelling from dual incision sites to anterior and posterior implantation sites with the cable extending subcutaneously tunnelled between the first and second hermetically sealed housings.

In a preferred embodiment, the first and second hermetically sealed housings have a length extending from a housing free end and a housing end attached to one end of the electrical cable, a housing width and a nominal housing thickness. The housing free ends are tapered from the nominal housing thickness to a lesser thickness to ease the subcutaneous advancement of the housing free ends to the first and second implantation sites.

Advantageously, the bulky and heavy components of the ICD circuitry are distributed between two hermetically sealed housings that can each be made smaller, thinner, and lighter than the single ICD IPG housing and can to support the first and second cardioversion/defibrillation electrodes as well as a sense electrode array and pacing electrodes.

The tethering cable can be disconnected from the first and/or second hermetically sealed housing to enable high voltage battery replacement and to facilitate tunneling of the tethering cable. Or the tethering cable can advantageously be permanently coupled to both hermetically sealed housings to eliminate bulky and expensive IPG and lead connector elements A third cardioversion electrode can advantageously be incorporated into the cable body.

Various functional configurations and capabilities can be incorporated into the ICD of the present invention. For example, the ICD capabilities can be restricted to simply providing cardioversion/defibrillation therapies as needed or can include various pacing therapies.

The maximum delivered cardioversion/defibrillation shock energy and high current battery life (as well as the delivered pacing pulse energy if pacing is included) can advantageously be specified to fit a particular patient profile. The shock energy (and pacing pulse energy) can be substantially reduced for pediatric patients, resulting in advantageously smaller volume and weight first and second hermetically sealed enclosures facilitating implantation. The shock energy and number of available shocks can also be limited for prophylactic implantation of the ICD in patients suspected to be at risk of sudden death.

Moreover, sensing of the far field EGM signals of interest is advantageously improved over the use of a single pair of EGM sense electrodes by use of the array of EGM sense electrodes.

The tether able can be very strong to withstand surgical trauma because the cable need not enter the vascular system like a traditional transvenous lead.

This summary of the invention and the advantages and features thereof have been presented here simply to point out some of the ways that the invention overcomes difficulties presented in the prior art and to distinguish the invention from the prior art and is not intended to operate in any manner as a limitation on the interpretation of claims that are presented initially in the patent application and that are ultimately granted.

BRIEF DESCRIPTION OF THE DRAWINGS

These and other advantages and features of the present invention will be appreciated as the same becomes better understood by reference to the following detailed description of the preferred embodiment of the invention when considered in connection with the accompanying drawings, in which like numbered reference numbers designate like parts throughout the figures thereof, and wherein.

DETAILED DESCRIPTION OF THE PREFERRED EMBODIMENTS

The present invention enables the implantation of an ICD subcutaneously in a wide variety of patients without having to surgically invade the thoracic cavity. The ICD comprises first and second hermetically sealed housings or cans that each bear a cardioversion/defibrillation electrode and that are coupled together by a cable enabling implantation of the first and second housings on opposite sides of the chest and heart. The first and second hermetically sealed housings and the cable can take any convenient shape. Therefore the illustrated shapes of the preferred embodiments are merely exemplary and are not intended to be limiting in any sense.

Figure 1:
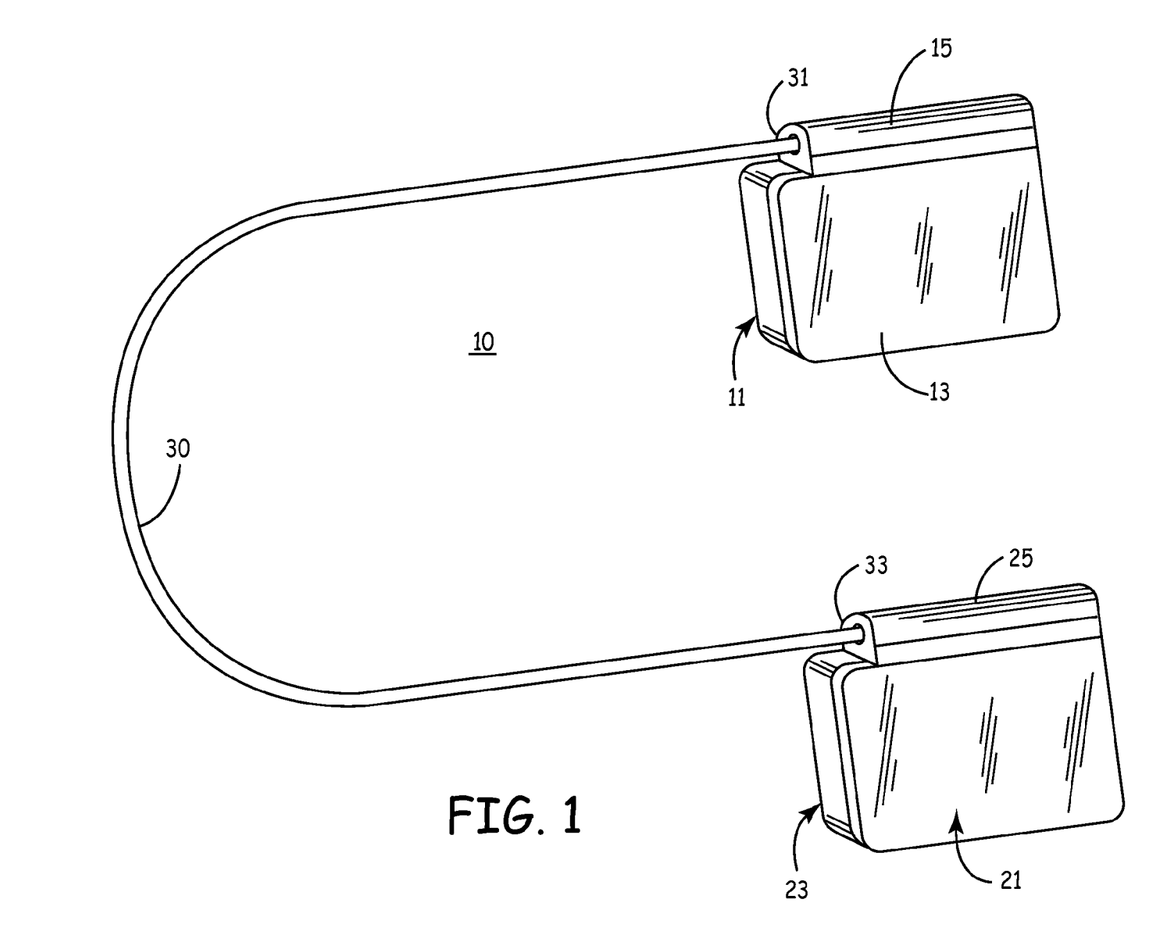
FIG. 1 is a perspective illustration of a first embodiment of an ICD in accordance with the present invention comprising first and second schematically depicted, hermetically sealed housings bearing first and second respective cardioversion/defibrillation electrodes, the housings tethered together by a cable.

FIG. 1 is a perspective illustration of a first embodiment of an ICD 10 in accordance with the present invention comprising first and second schematically depicted, hermetically sealed housings 11 and 21 tethered together by cable 30 and bearing first and second respective cardioversion/defibrillation electrodes 13 and 23 adapted to be implanted facing the heart. The hermetically sealed housing 11 encloses the electronic sensing, pacing, and cardioversion/defibrillation circuitry, including the relatively bulky high voltage capacitors that are charged and discharged to deliver cardioversion/defibrillation shocks, as well as a low voltage battery employed for powering the circuitry and the delivered pacing pulses. The second hermetically sealed housing 21 encloses a relatively bulky high power cardioversion/defibrillation battery as well as a switch to enable selective connection with the high voltage capacitor charging circuitry within the first housing in the manner described in the above-referenced '451 patent.

This switch might better be in housing 11 to eliminate control wires on the tether cable as the preferred embodiment. A minimum of 2 or 3 wires would be required in the tether, one for shock current delivery to the can, another to supply batter power + and a third to provide battery − that might be combined with the can as a ground.

The electrodes 13 and 23 can be between 100 mm$^2$ and 1000 mm$^2$, for example, and can be formed of a solid conductive sheet or a conductive mesh formed of a biocompatible electrode material, e.g., titanium, nickel alloys, stainless steel alloys, platinum, platinum iridium alloy, and mixtures thereof.

The cable 30 comprises an elongated cable body extending between cable ends 31 and 33 attached to the connector blocks 15 and 25 of the first and second hermetically sealed housings 11 and 21. The elongated cable body encloses four or five conductors that are separately insulated from one another and that are connected through feedthroughs in the connector block 15 to the electronic circuitry within the first hermetically sealed housing 11 at the first cable end 31. Four conductors within the cable body are connected to the second cardioversion/defibrillation electrode 23 or through feedthroughs in the connector block 25 to the high voltage battery or a switch described further below. The fifth conductor, if present, is connected to a pacing electrode on the surface of the second hermetically sealed housing 21, if present, as described further below.

Advantageously, the cable 30 is coupled to connector blocks 15 and 25 of hermetically sealed housings 11 and 21, respectively, in a conventional manner enabling the replacement of the first or second hermetically sealed housing 21 in the event that the high voltage battery becomes depleted as also described in the above-referenced '451 patent. Having a replaceable battery would benefit those pediatric patients or patients requiring lower cost ICDs described above who are dependent upon continued operation of the ICD. Alternatively, the cable 30 can be permanently attached at the cable first and second ends 31 and 33 to the first and/or second schematically depicted, hermetically sealed housings 11 and 21, if the ICD 10 is intended for prophylactic use and to be replaced after it is established that the patient is qualified for implantation of a more sophisticated longer-lived ICD.

Figure 2:
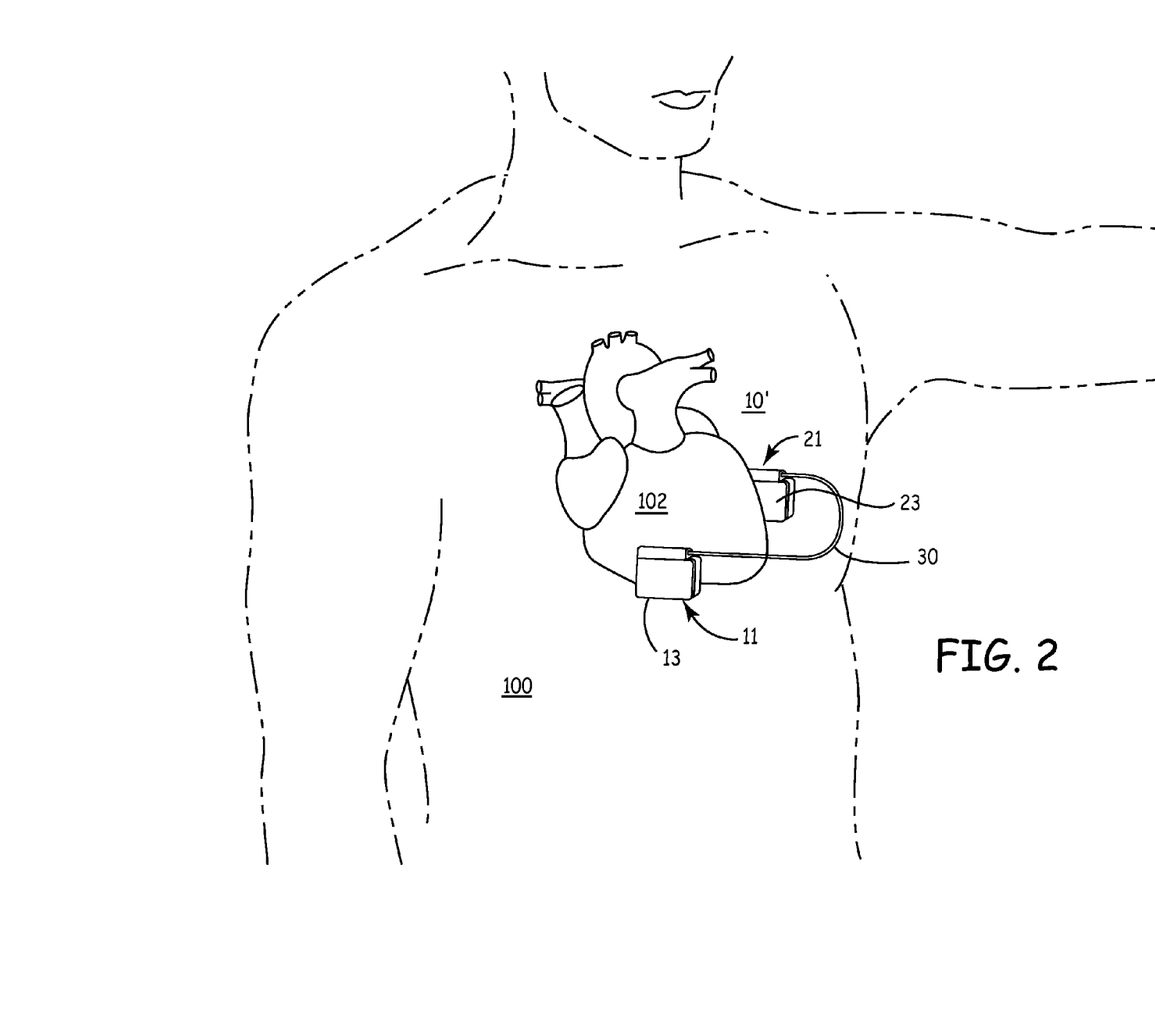
FIG. 2 is a schematic illustration of the ICD of FIG. 1 subcutaneously implanted in a patient's body outside the ribcage and in relation to the patient's heart.

The ICD 10 of FIG. 1 can be implanted subcutaneously in a patient's body 100, outside the thorax, yet inside the skin, as schematically illustrated in FIG. 2. The first and second respective cardioversion/defibrillation electrodes 13 and 23 are oriented toward one another and the heart 102 between the first and second schematically depicted, hermetically sealed housings 11 and 21. The first and second implantation sites can be anterior and posterior implantation sites between the third and twelfth ribs, for example.

The first and second implantation sites can include a posterior region of the patient's ribcage, a paraspinal region of the patient, a parascapular region of the patient, and approximately posterior to a mid axillary line of the patient.

Figure 3:
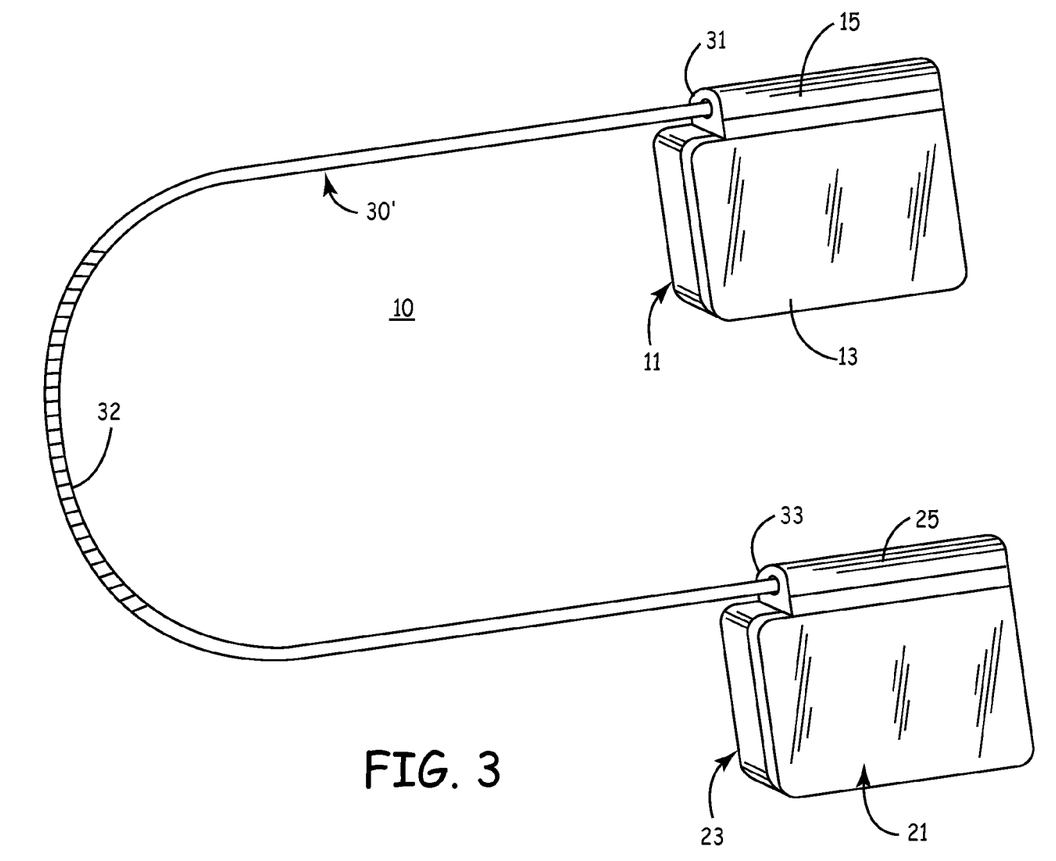
FIG. 3 is a perspective illustration of a second embodiment of an ICD in accordance with the present invention comprising first and second schematically depicted, hermetically sealed housings bearing first and second respective cardioversion/defibrillation electrodes, the housings tethered together by a cable, the cable bearing a third elongated cardioversion/defibrillation electrode.

The ICD embodiment of FIGS. 1 and 2, would deliver a monophasic or biphasic cardioversion/defibrillation shock of any of the known types to the heart 102 disposed between the large surface area, first and second cardioversion/defibrillation electrodes 13 and 23. It may be desirable to provide an additional discharge pathway for delivering the cardioversion/defibrillation shock to the heart 102. The ICD 10' of FIGS. 3 and 4 includes of a third, large surface area, cardioversion/defibrillation electrode 32 disposed along the length of the cable 30'. The elongated, flexible, third cardioversion/defibrillation electrode 32 may take any of the known forms that are typically employed on endocardial cardioversion/defibrillation leads and can be between five and ten centimetres long, for example. The elongated, flexible, third cardioversion/defibrillation electrode 32 is coupled via an additional conductor within the cable body extending to the cable end 31 to the electronic circuitry within the first hermetically sealed housing 11 through a further feedthrough in the connector header 15.

Figure 4:
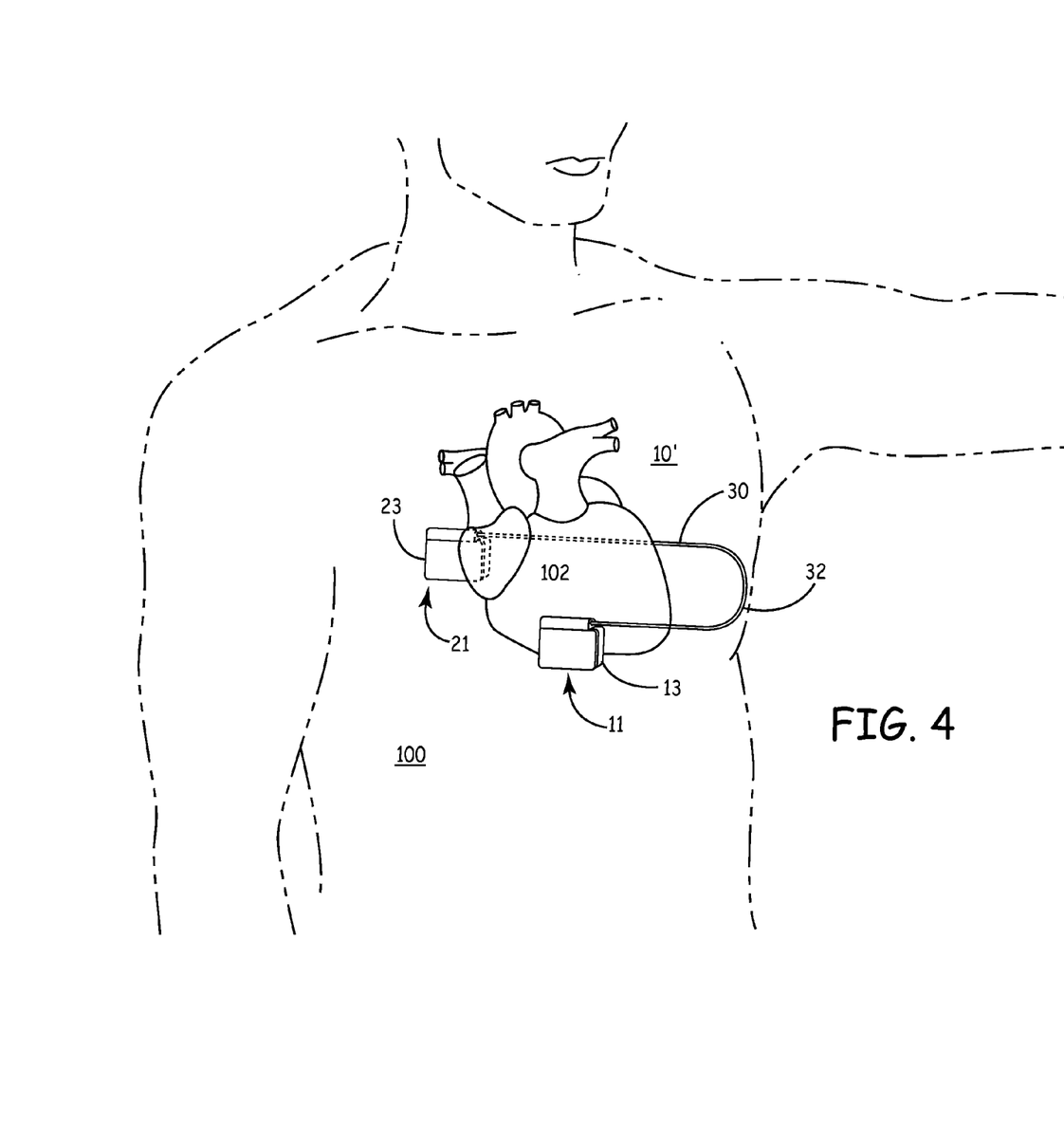
FIG. 4 is a schematic illustration of the ICD of FIG. 3 subcutaneously implanted in a patient's body outside the ribcage and in relation to the patient's heart.

When the ICD 10' is implanted as shown in FIG. 4, a cardioversion/defibrillation shocks could be delivered between the third cardioversion/defibrillation electrode 32 and the first and second cardioversion/defibrillation electrodes 13 and 23 connected together in common. Or, opposite polarity cardioversion/defibrillation shocks could be delivered simultaneously or sequentially between each of the first and second cardioversion/defibrillation electrodes 13 and 23 and the third cardioversion/defibrillation electrode 32.

The first and second hermetically sealed housings 11 and 21 of the first and second ICDs 10 and 10' are preferably implanted subcutaneously in posterior and anterior positions as illustrated in FIGS. 2 and 4 through a single skin incision intermediate the illustrated posterior and anterior positions. Tunnelling tools would be employed to displace the tissue and advance the first and second hermetically sealed housings 11 and 21 to the depicted sites or other selected sites around the thorax. Tissue adhesive may be employed to secure the first and second hermetically sealed housings 11 and 21 at the sites and prevent migration. Alternatively, the sites may be exposed through minimal surgical exposures, and the first and second hermetically sealed housings 11 and 21 can be sutured at the sites to prevent migration. Suture holes may be formed through the connector blocks 15 and 25 to facilitate such suturing to subcutaneous tissue or the ribs at the implantation sites.

Figure 5:
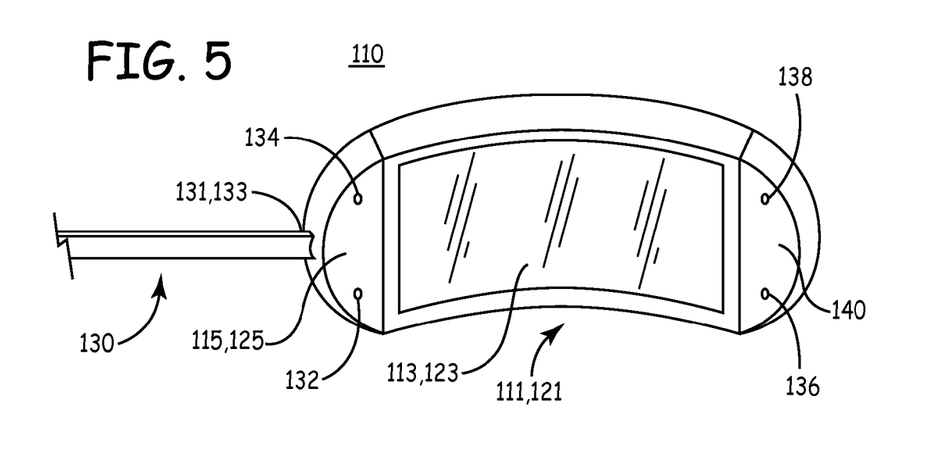
FIG. 5 is a plan view of the first and second ICD housing illustrating an array of sense electrodes for sensing the EGM usable in the ICD of the present invention.

The delivery of cardioversion/defibrillation shocks is dependent upon accurate sensing and reliable analysis of the signals of the EGM picked up from subcutaneous pace/sense electrodes mounted to one or both of the first and second schematically depicted, hermetically sealed housings 11 and 21. Preferably, EGM sensing is conducted from a two-dimensional array of EGM sense electrodes 22, 24 and 26 depicted on the surface of first hermetically sealed housing 11 and coupled to sensing circuitry within the first hermetically sealed housing 11 as shown in FIG. 5. Three-dimensional, far field EGM sensing can be provided by locating a fourth EGM sense electrode upon the opposite surface of first hermetically sealed housing 11 or a fourth EGM sense electrode can be formed on the surface of the second hermetically sealed housing 21. Multiple EGM vector signals in two or three dimensions can be developed by selectively pairing the EGM sense electrodes, measuring the signals and processing the measured signals in the manner described in commonly assigned U.S. Pat. No. 5,331,966.

One of the sense electrodes 22, 24, 26 can also function as a pacing electrode and can therefore be referred to as a first pace/sense electrode. Pacing would take place between the selected first pace/sense electrode 22, 24 or 26 and either the second cardioversion/defibrillation electrode 23 on the second hermetically sealed housing 21 or employing a second, small surface area, pacing electrode located on the surface of the second hermetically sealed housing 21 facing the heart. Alternatively, pacing pulses could be delivered between the large surface area, first and second cardioversion/defibrillation electrodes 13 and 23. Pacing pulses may have to be increased in energy, e.g., to a voltage of 50 volts, due to the dissipation of pacing pulse energy in the body tissue and fluids separating the selected pacing electrodes from the heart 102. The pacing pulses may be biphasic or monophasic having a peak voltage that is between about 5 volts and about 500 volts and a pulse width between about 2 milliseconds and about 40 milliseconds.

Although the sense electrodes 22, 24, 26 are depicted in FIG. 5 alongside the first cardioversion/defibrillation electrode 13, it will be understood that the sense electrodes 22, 24, 26 may be located on the opposite major side or about the minor sides of the first hermetically sealed housing 11 or about the connector block 15, and at least one of the sense electrodes 22, 24, 26 can be located on the electrical cable 30 or other locations as indicated in the above-referenced '966 patent.

The subcutaneous tunnelling to the implantation sites may be facilitated and the resulting cosmetic appearance may be improved by making the first and second hermetically sealed housings 11 and 21 as thin as possible, minimizing the bulk of the connector headers 15 and 25, and curving the major housing surfaces to conform well to the curvature of the thorax at recommended posterior and anterior or other implantation sites. In addition, fixation at the implantation sites may be facilitated by incorporating more suturing sites. Furthermore, the cable 30 may be flattened.

Figure 6:
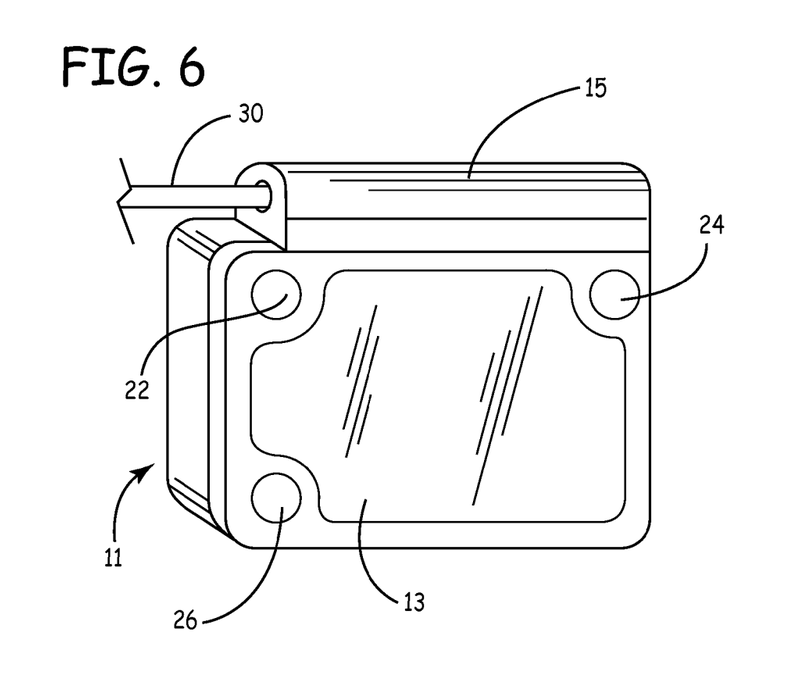
FIG. 6 is a plan view of one exemplary modification of the shapes of the first and second housings and the cables of the ICD embodiments of FIGS. 1–5.

The ICD 110 illustrated in part in FIG. 6 incorporates such features in the flattened, elongated, and concave curved first and second hermetically sealed housings 111 and 123 tethered together by cable 130. The elongated body of the cable 130 is somewhat flattened and may be formed with or without the elongated, flexible, third cardioversion/defibrillation electrode 132. It will be understood that electrical cable 130 is twisted 1800 as depicted in FIG. 6 to display the concave curved opposed major surfaces.

Each of the first and second hermetically sealed housings 111 and 121 is elongated, formed having somewhat concave curved opposed major surfaces, and is relatively thin. The first and second hermetically sealed housings 111 and 121 have a length extending from a housing free end and a housing end attached to the cable ends 131 and 133, respectively, a housing width and a nominal housing thickness. The housing free ends 140 and 142 are tapered from the nominal housing thickness to a lesser thickness. The tapered and curved free ends 140 and 142 of the first and second hermetically sealed housings 111 and 121, respectively, can be more readily advanced subcutaneously to the first and second implantation sites.

The connector headers 115, 125 that make either permanent or removable connections with the cable ends 131, 133 are formed as part of a first end section of the first and second hermetically sealed housings 111, 121. Suture holes 132, 134, 136 and 138 extend through the materials forming the tapered and curved connector header 115 and the free end section 140 of the first hermetically sealed housing 111. Suture holes 132', 134', 136' and 138' extend through the materials forming the tapered and curved connector header 125 and the free end section 142 of the second hermetically sealed housing 121. The ICD 110 can be implanted in the same manner as described above with respect to the ICDs 10 and 10' and depicted in FIGS. 2 and 4 but somewhat more easily because of the tapered shapes of the free end sections 140 and 142.

Again, EGM sensing is preferably conducted from a two-dimensional array of EGM sense electrodes 122, 124 and 126 depicted on the surface of first hermetically sealed housing 111 and coupled to sensing circuitry within the first hermetically sealed housing 111. One of the EGM sense electrodes 122, 124 and 126 can be employed as a pacing electrode. A further pace/sense electrode 128 is formed on the surface of the second hermetically sealed housing 121 as shown in FIG. 6 that is coupled to the pace/sense circuitry within the first hermetically sealed housing 111 by a conductor within cable 130.

Although the sense electrodes 122, 124, 126 are depicted in FIG. 6 alongside the first cardioversion/defibrillation electrode 113, it will be understood that the sense electrodes 122, 124, 126 may be located on the opposite major side or about the minor sides of the first hermetically sealed housing 111 or about the connector block 115, and at least one of the sense electrodes 122, 124, 126 can be located on the electrical cable 130 or other locations as indicated in the above-referenced '966 patent.

The cost of ICD 110 can be advantageously reduced for prophylactic use as described above by directly and permanently attaching (as by welding) the conductor ends at cable ends 131 and 133 directly to feedthrough pins of feedthroughs extending through the housing walls within the connector headers 115, 125. The connector headers 115 and 125 can simply be molded of thermoplastic resin over the feedthroughs.

Alternatively, the cable end 133 and the connector header 125 can be fabricated in a more conventional manner with mating connector elements. In this variation, the cable end 133 can be disconnected from a second hermetically sealed housing 121 containing a depleted high current battery and replaced with a new hermetically sealed housing 121 containing a fresh high current battery.

The electronic circuitry employed in the ICD 10 can take any of the known forms that detect a tachyarrhythmia from the sensed EGM and provide such cardioversion/defibrillation shocks as well as post-shock pacing as needed while the heart recovers. A simplified block diagram of such circuitry adapted to function employing the first and second and optionally the third cardioversion/defibrillation electrodes 13/113, 23/123 and 31/131 as well as the EGM sensing and pacing electrodes 22, 24, 26, 28 described above is set forth in FIG. 7. It will be understood that the simplified block diagram does not show all of the conventional components and circuitry of such ICDs including digital clocks and clock lines, low voltage power supply and supply lines for powering the circuits and providing pacing pulses or telemetry circuits for telemetry transmissions between the ICD and an external programmer or monitor.

Figure 7:
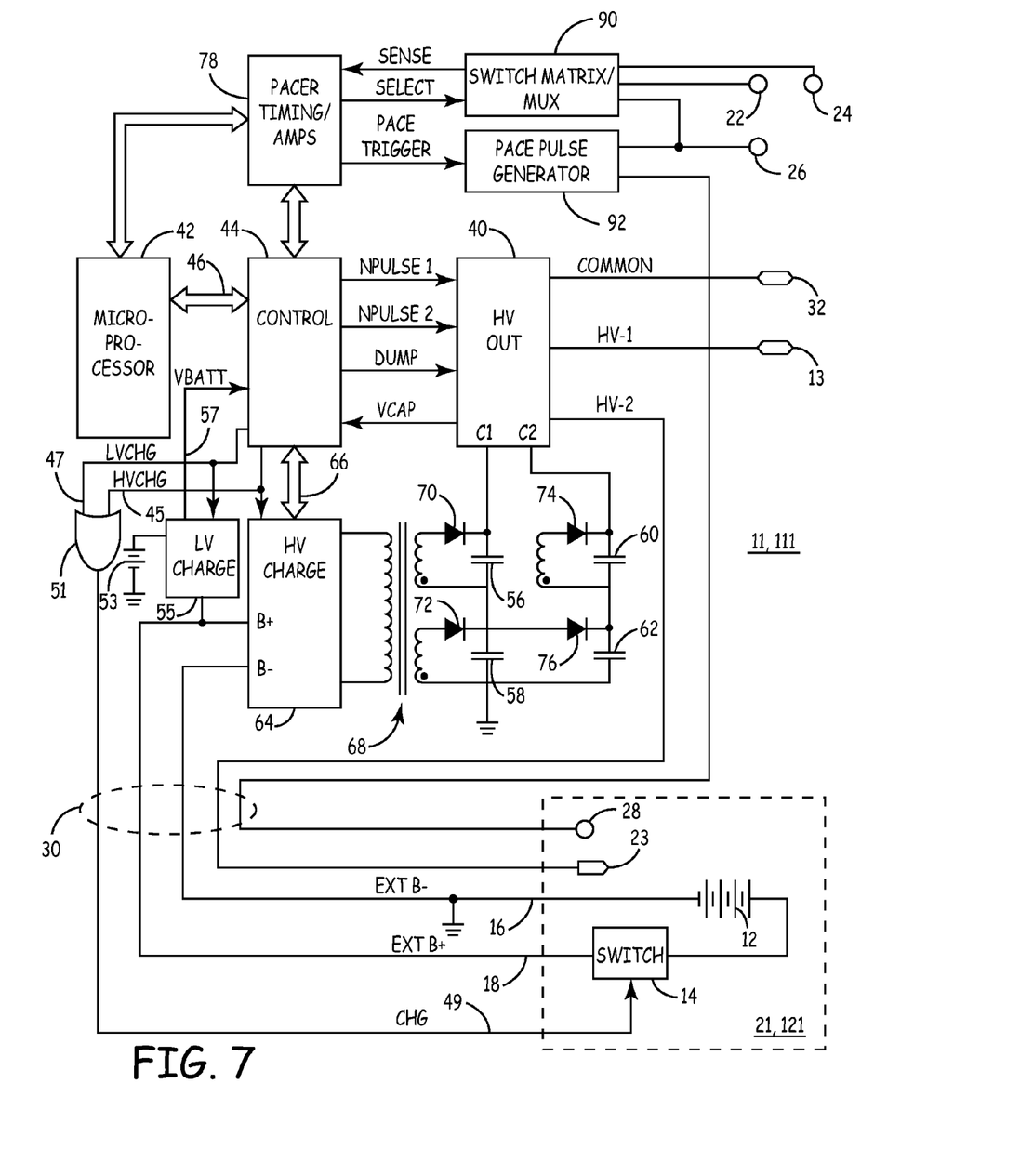
FIG. 7 is a block diagram of a preferred embodiment of the circuitry of the ICD of FIGS. 1–6.

FIG. 7 depicts the electronic circuitry and low voltage battery 53 within the first hermetically sealed housing 11/111, as well as the high current battery 12 and a power switch circuit 14 within the second hermetically sealed housing 21/121, depicted within broken lines, although power switch circuit 14 may be positioned within housing 11/111. The low voltage battery 53 is coupled to a power supply (not shown) that supplies power to the ICD circuitry and the pacing output capacitors to supply pacing energy in a manner well known in the art. The low voltage battery can comprise one or two conventional LiCFx cells. The high voltage battery 12 can comprise one or two conventional LiSVO or $LiMnO_2$ cell.

The sense electrodes 22, 24, 26 and the first cardioversion/defibrillation electrode 13/113 on the surface of the first hermetically sealed housing 11/111 are depicted in FIG. 7 coupled directly with the electronic circuitry within the first hermetically sealed housing 11/111. The cable 30/130 is depicted coupling the high voltage battery 12 and switching circuit 14 with the electronic circuitry within the first hermetically sealed housing 11/111 through cable conductors 16, 18 and 49. A pace/sense electrode 28 and the second cardioversion/defibrillation electrode 23/123 located on the surface of the second hermetically sealed housing 21/121 are depicted in FIG. 7 coupled with the electronic circuitry within the first hermetically sealed housing 11/111 via conductors 17 and 19, respectively, of cable 32/132. Conductor 17 can be employed and characterized as a pacing conductor when pace/sense electrode 28 is simply used as pacing electrode or as a sensing conductor when pace/sense electrode 28 is simply used as a far field EGM sense electrode. A cardioversion/defibrillation conductor 45 extends from the elongated third cardioversion/defibrillation electrode 32/132 mounted on cable 30/130 to the electronic circuitry within the first hermetically sealed housing 11/111, particularly the high voltage output circuit 40.

In FIG. 7, ICD functions are controlled by means of stored software, firmware and hardware that cooperatively monitor the EGM, determine when a cardioversion/defibrillation shock or pacing is necessary, and deliver prescribed cardioversion/defibrillation and pacing therapies. The block diagram of FIG. 7 incorporates circuitry set forth in the above-referenced '451 application and commonly assigned U.S. Pat. Nos. 5,163,427 and 5,188,105 for selectively delivering single, phase, simultaneous biphasic and sequential biphasic cardioversion/defibrillation shocks typically employing an ICD IPG housing electrode coupled to the COMMON output of high voltage output circuit 40 and two cardioversion/defibrillation electrodes disposed in a heart chamber or cardiac vessel coupled to the HV1 and HV-2 outputs of the high voltage output circuit 40. The circuitry of the subcutaneous ICDs of the present invention can be made simpler by adoption of one such cardioversion/defibrillation shock waveform for delivery simply between the first and second cardioversion/defibrillation electrodes 13/113 and 23/132 coupled to the HV-1 and HV-2 outputs respectively. Or, the third cardioversion/defibrillation electrode 32/132 can be coupled to the COMMON output as depicted in FIG. 7 and the first and second cardioversion/defibrillation electrodes 13/113 and 23/132 can be electrically connected in to the HV-1 and the HV-2 outputs, respectively, as depicted in FIG. 7.

The cardioversion/defibrillation shock energy and capacitor charge voltages can be intermediate to those supplied by ICDs having at least one cardioversion/defibrillation electrode in contact with the heart and most AEDs having cardioversion/defibrillation electrodes in contact with the skin. The typical maximum voltage necessary for ICDs using most biphasic waveforms is approximately 750 Volts with an associated maximum energy of approximately 40 Joules. The typical maximum voltage necessary for AEDs is approximately 2000–5000 Volts with an associated maximum energy of approximately 200–360 Joules depending upon the model and waveform used. The ICD of the present invention uses maximum voltages in the range of about 700 to about 3150 Volts and is associated with energies of about 25 Joules to about 210 Joules. The total high voltage capacitance could range from about 50 to about 300 microfarads.

Such cardioversion/defibrillation shocks are only delivered when a malignant tachyarrhythmia, e.g., ventricular fibrillation is detected through processing of the far field cardiac EGM employing one of the available detection algorithms known in the ICD art. In FIG. 7, pacer timing/ sense amplifier circuit 78 processes the far field EGM SENSE signals that are developed across a particular EGM sense vector defined by a selected pair of the sense electrodes 22, 24, 26 and optionally pace/sense electrode 28 if present on the second hermetically sealed housing 21/121 or the second cardioversion/defibrillation electrode 23/123 as noted above. The selection of the sense electrode pair is made through the switch matrix/MUX 90 in a manner disclosed in the above-referenced '966 patent to provide the most reliable sensing of the EGM signal of interest, which would be the R-wave for patients who are believed to be at risk of ventricular fibrillation leading to sudden death. The far field EGM signals are passed through the switch matrix/ MUX 90 to the input of a sense amplifier in the pacer timing/sense amplifier circuit 78.

Bradycardia is typically determined by an escape interval timer within the pacer timing circuit 78 or the timing and control circuit 44, and pacing pulses that develop a PACE TRIGGER signal applied to the pacing pulse generator 92 when the interval between successive R-waves exceeds the escape interval. Bradycardia pacing is often provided to maintain cardiac output after delivery of a cardioversion/defibrillation shock that may cause the heart to slowly beat as it recovers function.

Detection of a malignant tachyarrhythmia is determined in the timing and control circuit 44 as a function of the intervals between R-wave sense event signals that are output from the pacer timing/sense amplifier circuit 78 to the timing and control circuit 44. Certain steps in the performance of the detection algorithm criteria are cooperatively performed in a microcomputer 42, including microprocessor, RAM and ROM, associated circuitry, and stored detection criteria that may be programmed into RAM via a telemetry interface (not shown) conventional in the art. Data and commands are exchanged between microcomputer 42 and timing and control circuit 44, pacer timing/amplifier circuit 78, and high voltage output circuit 40 via a bidirectional data/control bus 46. The pacer timing/amplifier circuit 78 and the timing and control circuit 44 are clocked at a slow clock rate. The microcomputer 42 is normally asleep, but is awakened and operated by a fast clock by interrupts developed by each R-wave sense event or on receipt of a downlink telemetry programming instruction or upon delivery of cardiac pacing pulses to perform any necessary mathematical calculations, to perform tachycardia and fibrillation detection procedures, and to update the time intervals monitored and controlled by the timers in pace/sense circuitry 78. The algorithms and functions of the microcomputer 42 and timer and control circuit 44 employed and performed in detection of tachyarrhythmias are set forth, for example, in commonly assigned U.S. Pat. Nos. 5,991,656 and 5,193,535, for example. Particular algorithms for detection of ventricular fibrillation and malignant ventricular tachycardias can be selected from among the comprehensive algorithms for distinguishing atrial and ventricular tachyarrhythmias from one another and from high rate sinus rhythms that are set forth in the '656 and '535 patents.

The detection algorithms are highly sensitive and specific for the presence or absence of life threatening ventricular arrhythmias, e.g., ventricular tachycardia (V-TACH) and ventricular fibrillation (V-FIB). Another optional aspect of the present invention is that the operational circuitry can detect the presence of atrial fibrillation (A-FIB) as described in Olson, W. et al. "Onset And Stability For Ventricular Tachyarrhythmia Detection in an Implantable Cardioverter and Defibrillator," *Computers in Cardiology* (1986) pp. 167–170. Detection can be provided via R—R Cycle length instability detection algorithms. Once A-FIB has been detected, the operational circuitry will then provide QRS synchronized atrial cardioversion/defibrillation using the same shock energy and wave shapes used for ventricular cardioversion/defibrillation.

Operating modes and parameters of the detection algorithm are programmable and the algorithm is focused on the detection of V-FIB and high rate V-TACH (>240 bpm). Although the ICD of the present invention may rarely be used for an actual sudden death event, the simplicity of design and implementation allows it to be employed in large populations of patients at modest risk with modest cost by medical personnel other than electrophysiologists. Consequently, the ICD of the present invention includes the automatic detection and therapy of the most malignant rhythm disorders. As part of the detection algorithm's applicability to children, the upper rate range is programmable upward for use in children, known to have rapid supraventricular tachycardias and more rapid V-FIB.

When a malignant tachycardia is detected, high voltage capacitors 56, 58, 60, and 62 are charged to a pre-programmed voltage level by a high-voltage charging circuit 64. It is generally considered inefficient to maintain a constant charge on the high voltage output capacitors 56, 58, 60, 62. Instead, charging is initiated when control circuit 44 issues a high voltage charge command HVCHG delivered on line 45 to high voltage charge circuit 64 and charging is controlled by means of bidirectional control/data bus 66 and a feedback signal VCAP from the HV output circuit 40.

Preferably, the positive and negative terminals of the high current battery are not electrically connected to the high voltage charge circuit terminals B+ and B− at all times. The negative terminal of high voltage battery 12 is directly coupled to system ground and to the negative power input of the high voltage charge circuit 64 through EXT B−conductor 16. Switch circuit 14 is normally open so that the positive terminal of high voltage battery 12 is disconnected from EXT B+conductor 18 and the positive power input of the high voltage charge circuit 64. The high voltage charge command HVCHG is also conducted via conductor 49 to the control input of switch circuit 14, and switch circuit 14 closes in response to connect positive high voltage battery voltage EXT B+ to the positive power input of high voltage charge circuit 64. Switch circuit 14 may be, for example, a field effect transistor (FET) with its source-to-drain path interrupting the EXT B+ conductor 18 and its gate receiving the HVCHG signal on conductor 45. High voltage charge circuit 64 is thereby rendered ready to begin charging the high voltage output capacitors 56, 58, 60, and 62 with charging current from high voltage battery 12. It will be understood that the switch circuit 14 can be included with the circuitry enclosed within the first hermetically sealed enclosure 11/111 at the B+ terminal of the high voltage charging circuit 64 rather than in the second hermetically sealed enclosure 21/121. In this case, the cable conductor 49 could advantageously be eliminated from cable 30/130.

High voltage output capacitors 56, 58, 60, and 62 may be charged to very high voltages, e.g., 700–3150V, to be discharged through the body and heart between the selected electrode pairs among first, second, and, optionally, third subcutaneous cardioversion/defibrillation electrodes 13/113, 12/123, and 32/132. The details of the voltage charging circuitry are also not deemed to be critical with regard to practicing the present invention; one high voltage charging circuit believed to be suitable for the purposes of the present invention is disclosed High voltage capacitors 56, 58, 60, and 62 are charged by high voltage charge circuit 64 and a high-frequency, high-voltage transformer 68 as described in detail in commonly assigned U.S. Pat. No. 4,548,209. Proper charging polarities are maintained by diodes 70, 72, and 74 interconnecting the output windings of high-voltage transformer 68 and the capacitors 56, 58, 60, and 62. As noted above, the state of capacitor charge is monitored by circuitry within the high voltage output circuit 40 that provides a VCAP feedback signal indicative of the voltage to the timing and control circuit 44. Timing and control circuit 44 terminates the high voltage charge command HVCHG when the VCAP signal matches the programmed capacitor output voltage, i.e., the cardioversion/defibrillation peak shock voltage.

Timing and control circuit 44 then develops first and second control signals NPULSE 1 and NPULSE 2, respectively, that are applied to the high voltage output circuit 40 for triggering the delivery of cardioverting or defibrillating shocks. In particular, the NPULSE 1 signal triggers discharge of the first capacitor bank, comprising capacitors 56 and 58. The NPULSE 2 signal triggers discharge of the first capacitor bank and a second capacitor bank, comprising capacitors 60 and 62. It is possible to select between a plurality of output pulse regimes simply by modifying the number and time order of assertion of the NPULSE 1 and NPULSE 2 signals. The NPULSE-1 signals and NPULSE-2 signals may be provided sequentially, simultaneously or individually. In this way, control circuitry 44 serves to control operation of the high voltage output stage 40, which delivers high energy cardioversion/defibrillation shocks between a selected pair or pairs of the first, second, and, optionally, the third cardioversion/defibrillation electrodes 13/113, 23/123, and 32/132 coupled to the HV-1, HV-2 and optionally to the COMMON output as shown in FIG. 7.

Thus, ICD 10/110 monitors the patient's cardiac status and initiates the delivery of a cardioversion/defibrillation shock through a selected pair or pairs of the first, second and third cardioversion/defibrillation electrodes 13/113, 23/123 and 32/132 in response to detection of a tachyarrhythmia requiring cardioversion/defibrillation. The high HVCHG signal causes the high voltage battery 12 to be connected through the switch circuit 14 and cable 30/130 with the high voltage charge circuit 64 and the charging of output capacitors 56, 58, 60, and 62 to commence. Charging continues until the programmed charge voltage is reflected by the VCAP signal, at which point control and timing circuit 44 sets the HVCHG signal low terminating charging and opening switch circuit 14. Typically, the charging cycle takes only fifteen to twenty seconds, and occurs very infrequently. Except during the relatively short charging cycle, there is no voltage differential between the EXT B+ and EXT B− conductors 16 and 18, and high voltage battery leakage current is minimized.

The ICD 10, 110 can be programmed to attempt to deliver cardioversion shocks to the heart in the manners described above in timed synchrony with a detected R-wave or can be programmed or fabricated to deliver defibrillation shocks to the heart in the manners described above without attempting to synchronize the delivery to a detected R-wave. Episode data related to the detection of the tachyarrhythmia and delivery of the cardioversion/defibrillation shock can be stored in RAM for uplink telemetry transmission to an external programmer as is well known in the art to facilitate in diagnosis of the patient's cardiac state. A patient receiving the ICD 10, 110 on a prophylactic basis would be instructed to report each such episode to the attending physician for further evaluation of the patient's condition and assessment for the need for implantation of a more sophisticated and long-lived ICD.

As noted above, for longer-term implants, the second hermetically sealed enclosure 21/121 can include a connector block that enables removal from the cable end 33/133 when the high voltage battery 12 is depleted so that the new hermetically sealed enclosure 21/121 can be easily replaced.

All patents and printed publications disclosed herein are hereby incorporated by reference herein into the specification hereof, each in its respective entirety.

What is claimed is:

1. In an implantable cardioverter/defibrillator of the type comprising a plurality of components including a relatively bulky high voltage battery, at least one high voltage capacitor, and circuitry powered by a low voltage power source for detecting a tachyarrhythmia, charging the high voltage capacitor, and discharging the high voltage capacitor to provide a cardioversion/defibrillation shock, the improvement comprising:
    a first hermetically sealed housing supporting a first cardioversion/defibrillation electrode adapted to be implanted at a first subcutaneous implantation site about the patient's thorax directing the first cardioversion/defibrillation electrode toward the patient's heart;
    a second hermetically sealed housing supporting a second cardioversion/defibrillation electrode adapted to be implanted at a second subcutaneous implantation site about the patient's thorax directing the second cardioversion/defibrillation electrode toward the patient's heart, whereby the heart is disposed substantially between the first and second cardioversion/defibrillation electrodes; and
    an electrical cable having a plurality of conductors tethering the first and second hermetically sealed housings together,
    wherein the components of the ICD are distributed between the first and second hermetically sealed housings, and conductors of the electrical cable interconnect the components to enable generation and delivery of cardioversion/defibrillation shocks between the first and second cardioversion/defibrillation electrodes and across the patient's heart.

2. The implantable cardioverter/defibrillator of claim 1, wherein the high voltage battery is enclosed within the second hermetically sealed housing.

3. The implantable cardioverter/defibrillator of claim 2, wherein:
    the at least one high voltage capacitor and the circuitry powered by the low voltage power source for detecting a tachyarrhythmia, charging the high voltage capacitor, and discharging the high voltage capacitor to provide a cardioversion/defibrillation shock are enclosed within the first hermetically sealed housing; and
    the high voltage battery is coupled through conductors of the cable to the circuitry for charging the high voltage capacitor.

4. The implantable cardioverter/defibrillator of claim 3, further comprising a switch circuit between the high voltage battery and the circuitry for charging the high voltage capacitor that is adapted to be closed to enable charging the high voltage capacitor.

5. The implantable cardioverter/defibrillator of claim 1, wherein the electrical cable is coupled at a first cable end to the first hermetically sealed housing and at a second cable end to the second hermetically sealed housing, and at least one of the first and second cable ends can be disconnected from the respective first and second hermetically sealed housings to enable replacement of the second hermetically sealed enclosure upon depletion of the high voltage battery.

6. The implantable cardioverter/defibrillator of claim 1, wherein the electrical cable is permanently coupled at a first cable end to the first hermetically sealed housing and at a second cable end to the second hermetically sealed housing.

7. The implantable cardioverter/defibrillator of claim 1, wherein:
    the first hermetically sealed housing supports a two-dimensional array of far-field EGM sense electrodes defining a plurality of EGM sense vectors; and
    the circuitry further comprises a sense amplifier for sensing a signal of the cardiac EGM and a selection circuit for coupling the sense amplifier to the array of far-field sense electrodes to sense the EGM in a selected EGM sense vector.

8. The implantable cardioverter/defibrillator of claim 1, wherein:
the first hermetically sealed housing supports a first pacing electrode;
the second hermetically sealed housing supports a second pacing electrode;
the circuitry further comprises a pacing pulse generator for generating pacing pulses, the pacing pulse generator coupled to the first pacing electrode; and
the cable comprises a pacing conductor coupled between the pacing pulse generator and the second pacing electrode, whereby the pacing pulse generator generates pacing pulses that are delivered to the heart between the first and second pacing electrodes.

9. The implantable cardioverter/defibrillator of claim 1, wherein:
the cable supports a third cardioversion/defibrillation electrode and a cardioversion/defibrillation conductor coupled to the third cardioversion/defibrillation electrode; and
the circuitry for discharging the high voltage capacitor to provide a cardioversion/defibrillation shock is coupled to the cardioversion/defibrillation conductor and further comprises means for selectively delivering cardioversion/defibrillation shocks among selected pairs of the first, second and third cardioversion/defibrillation electrodes.

10. The implantable cardioverter/defibrillator of claim 9, further comprising means for selectively delivering cardioversion/defibrillation shocks having one of a monophasic waveform or a biphasic waveform.

11. An implantable cardioverter/defibrillator comprising:
a first hermetically sealed housing supporting a first cardioversion/defibrillation electrode adapted to be implanted at a first subcutaneous implantation site about the patient's thorax directing the first cardioversion/defibrillation electrode toward the patient's heart;
a second hermetically sealed housing supporting a second cardioversion/defibrillation electrode adapted to be implanted at a second subcutaneous implantation site about the patient's thorax directing the second cardioversion/defibrillation electrode toward the patient's heart, whereby the heart is disposed substantially between the first and second cardioversion/defibrillation electrodes;
a high voltage battery enclosed within the second hermetically sealed housing;
cardioversion/defibrillation shock generating means enclosed within the first hermetically sealed housing coupled to the first cardioversion/defibrillation electrode;
an electrical cable tethering the first and second hermetically sealed housings together and electrically connecting the high voltage battery and the second cardioversion/defibrillation electrode to the cardioversion/defibrillation shock generating means; and
means for triggering generation and delivery of cardioversion/defibrillation shocks between the first and second cardioversion/defibrillation electrodes and across the patient's heart.

12. The implantable cardioverter/defibrillator of claim 11 wherein the means for triggering generation and delivery of cardioversion/defibrillation shocks further comprises a plurality of components including at least one high voltage capacitor, and circuitry powered by a low voltage power source for detecting a tachyarrhythmia, charging the high voltage capacitor, and discharging the high voltage capacitor to provide a cardioversion/defibrillation shock all enclosed within the first hermetically sealed enclosure.

13. The implantable cardioverter/defibrillator of claim 12, wherein:
the at least one high voltage capacitor and the circuitry powered by the low voltage power source for detecting a tachyarrhythmia, charging the high voltage capacitor, and discharging the high voltage capacitor to provide a cardioversion/defibrillation shock are enclosed within the first hermetically sealed housing; and
the high voltage battery is coupled through conductors of the cable to the circuitry for charging the high voltage capacitor.

14. The implantable cardioverter/defibrillator of claim 13, further comprising a switch circuit between the high voltage battery and the circuitry for charging the high voltage capacitor that is adapted to be closed to enable charging the high voltage capacitor.

15. The implantable cardioverter/defibrillator of claim 12, wherein the electrical cable is coupled at a first cable end to the first hermetically sealed housing and at a second cable end to the second hermetically sealed housing, and at least one of the first and second cable ends can be disconnected from the respective first and second hermetically sealed housings to enable replacement of the second hermetically sealed enclosure upon depletion of the high voltage battery.

16. The implantable cardioverter/defibrillator of claim 12, wherein the electrical cable is permanently coupled at a first cable end to the first hermetically sealed housing and at a second cable end to the second hermetically sealed housing.

17. The implantable cardioverter/defibrillator of claim 12, wherein:
the first hermetically sealed housing supports a two-dimensional array of far-field EGM sense electrodes defining a plurality of EGM sense vectors; and
the circuitry further comprises a sense amplifier for sensing a signal of the cardiac EGM and a selection circuit for coupling the sense amplifier to the array of far-field sense electrodes to sense the EGM in a selected EGM sense vector.

18. The implantable cardioverter/defibrillator of claim 12, wherein:
the first hermetically sealed housing supports a first pacing electrode;
the second hermetically sealed housing supports a second pacing electrode;
the circuitry further comprises a pacing pulse generator for generating pacing pulses, the pacing pulse generator coupled to the first pacing electrode; and
the cable comprises a pacing conductor coupled between the pacing pulse generator and the second pacing electrode, whereby the pacing pulse generator generates pacing pulses that are delivered to the heart between the first and second pacing electrodes.

19. The implantable cardioverter/defibrillator of claim 12, wherein:
the cable supports a third cardioversion/defibrillation electrode and a cardioversion/defibrillation conductor coupled to the third cardioversion/defibrillation electrode; and
the circuitry for discharging the high voltage capacitor to provide a cardioversion/defibrillation shock is coupled to the cardioversion/defibrillation conductor and further comprises means for selectively delivering cardioversion/defibrillation shocks among selected pairs of the first, second and third cardioversion/defibrillation electrodes.

20. The implantable cardioverter/defibrillator of claim 19, further comprising means for selectively delivering cardioversion/defibrillation shocks having one of a monophasic waveform or a biphasic waveform.

21. The implantable cardioverter/defibrillator of claim 11, wherein the electrical cable is coupled at a first cable end to the first hermetically sealed housing and at a second cable end to the second hermetically sealed housing, and at least one of the first and second cable ends can be disconnected from the respective first and second hermetically sealed housings to enable replacement of the second hermetically sealed enclosure upon depletion of the high voltage battery.

22. The implantable cardioverter/defibrillator of claim 11, wherein the electrical cable is permanently coupled at a first cable end to the first hermetically sealed housing and at a second cable end to the second hermetically sealed housing.

23. The implantable cardioverter/defibrillator of claim 11, wherein:
  the first and second hermetically sealed housings have a length extending from a housing free end and a housing end attached to one end of the electrical cable, a housing width and a nominal housing thickness; and
  the housing free ends are tapered from the nominal housing thickness to a lesser thickness to ease the subcutaneous advancement of the housing free ends to the first and second implantation sites.

* * * * *